US012083087B2

(12) United States Patent
Jacobsen

(10) Patent No.: US 12,083,087 B2
(45) Date of Patent: *Sep. 10, 2024

(54) AQUEOUS FORMULATION COMPRISING PARACETAMOL AND IBUPROFEN

(71) Applicant: Hyloris Pharmaceuticals SA, Liege (BE)

(72) Inventor: Thomas Jacobsen, Liège (BE)

(73) Assignee: Hyloris Pharmaceuticals SA, Liege (BE)

( * ) Notice: Subject to any disclaimer, the term of this patent is extended or adjusted under 35 U.S.C. 154(b) by 0 days.

This patent is subject to a terminal disclaimer.

(21) Appl. No.: 17/867,370

(22) Filed: Jul. 18, 2022

(65) Prior Publication Data

US 2023/0181502 A1 Jun. 15, 2023

Related U.S. Application Data

(60) Continuation of application No. 17/502,899, filed on Oct. 15, 2021, now Pat. No. 11,389,416, which is a continuation of application No. 16/424,274, filed on May 28, 2019, now Pat. No. 11,213,498, which is a division of application No. 15/326,958, filed as application No. PCT/EP2015/066466 on Jul. 17, 2015, now Pat. No. 11,219,609.

(30) Foreign Application Priority Data

Jul. 18, 2014 (WO) ................ PCT/EP2014/065544

(51) Int. Cl.
| | |
|---|---|
| *A61K 31/192* | (2006.01) |
| *A61J 1/10* | (2006.01) |
| *A61J 1/20* | (2006.01) |
| *A61K 9/00* | (2006.01) |
| *A61K 9/08* | (2006.01) |
| *A61K 31/167* | (2006.01) |
| *A61K 47/20* | (2006.01) |
| *A61K 47/26* | (2006.01) |
| *A61M 5/14* | (2006.01) |
| *A61M 5/19* | (2006.01) |

(52) U.S. Cl.
CPC .............. *A61K 31/192* (2013.01); *A61J 1/10* (2013.01); *A61J 1/2093* (2013.01); *A61K 9/0019* (2013.01); *A61K 9/08* (2013.01); *A61K 31/167* (2013.01); *A61K 47/20* (2013.01); *A61K 47/26* (2013.01); *A61M 5/1407* (2013.01); *A61M 5/19* (2013.01)

(58) Field of Classification Search
CPC ...... A61K 31/192; A61K 9/0019; A61K 9/08; A61K 31/167; A61K 47/20; A61K 47/26; A61J 1/10; A61J 1/2093; A61M 5/1407; A61M 5/19
See application file for complete search history.

(56) References Cited

U.S. PATENT DOCUMENTS

| | | | |
|---|---|---|---|
| 11,389,416 | B2 | 7/2022 | Jacobsen |
| 11,413,241 | B2 | 8/2022 | Jacobsen |
| 2004/0054012 | A1* | 3/2004 | Dietlin ................. A61K 31/167 514/646 |
| 2006/0100578 | A1 | 5/2006 | Lieberman |
| 2011/0039939 | A1 | 2/2011 | Al Dandachi Atassi |
| 2012/0035267 | A1* | 2/2012 | Dasberg ............... A61K 31/167 514/630 |
| 2013/0210922 | A1* | 8/2013 | Tseti .................... A61K 9/0019 514/629 |
| 2013/0225685 | A1* | 8/2013 | Atkinson ............. A61K 9/0019 514/570 |
| 2013/0245591 | A1* | 9/2013 | Pavliv .................. A61K 9/0019 604/408 |
| 2017/0209398 | A1 | 7/2017 | Jacobson |
| 2019/0343785 | A1 | 11/2019 | Jacobson |
| 2022/0031645 | A1 | 2/2022 | Jacobsen |

FOREIGN PATENT DOCUMENTS

| | | |
|---|---|---|
| BE | 1020614 | 1/2014 |
| CN | 103298464 | 9/2013 |
| EP | 2620124 | 7/2013 |
| JP | 2011-508768 | 3/2011 |
| JP | 2012-505830 | 3/2012 |
| JP | 2012-524738 | 10/2012 |
| JP | 2013-541583 | 11/2013 |
| WO | WO 2009/083759 | 7/2009 |
| WO | WO 2010/044681 | 4/2010 |
| WO | WO 2010/121762 | 10/2010 |
| WO | WO 2011/018522 | 2/2011 |
| WO | WO 2012/060719 | 5/2012 |
| WO | WO 2013/138628 | 9/2013 |
| WO | WO 2016/008546 | 1/2016 |

OTHER PUBLICATIONS

Fairbrother, "Acetaminophen," Analytical Profiles of Drug Substances, 1974, 3, 1-109.
Koshy et al., "Stability of aqueous solutions of N-acetyl-p-aminophenol," Journal of Pharmaceutical Sciences, Feb. 1, 1961, 50(2):113-8.
Shaw et al., "The Effect of Selected Water-Soluble Excipients on the Dissolution of Paracetamol and Ibuprofen," Drug Development and Industrial Pharmacy, vol. 31(6), pp. 515-525 (Jul. 1, 2005).
Yasmeen et al., "Dissolution Method Development and Validation for Combination of Ibuprofen and Paracetamol Tablets," Asian Journal of Pharmaceutical and Clinical Research. vol. 6, Suppl 2, 2013.

* cited by examiner

*Primary Examiner* — Jeffrey S Lundgren
*Assistant Examiner* — Ibrahim D Bori
(74) *Attorney, Agent, or Firm* — Fish & Richardson P.C.

(57) ABSTRACT

An aqueous ibuprofen and paracetamol composition has a pH 6.3-7.3. The composition can be used as a medicament, especially for the treatment of pain and/or inflammation. The composition can be formulated for intravenous injection.

8 Claims, 1 Drawing Sheet

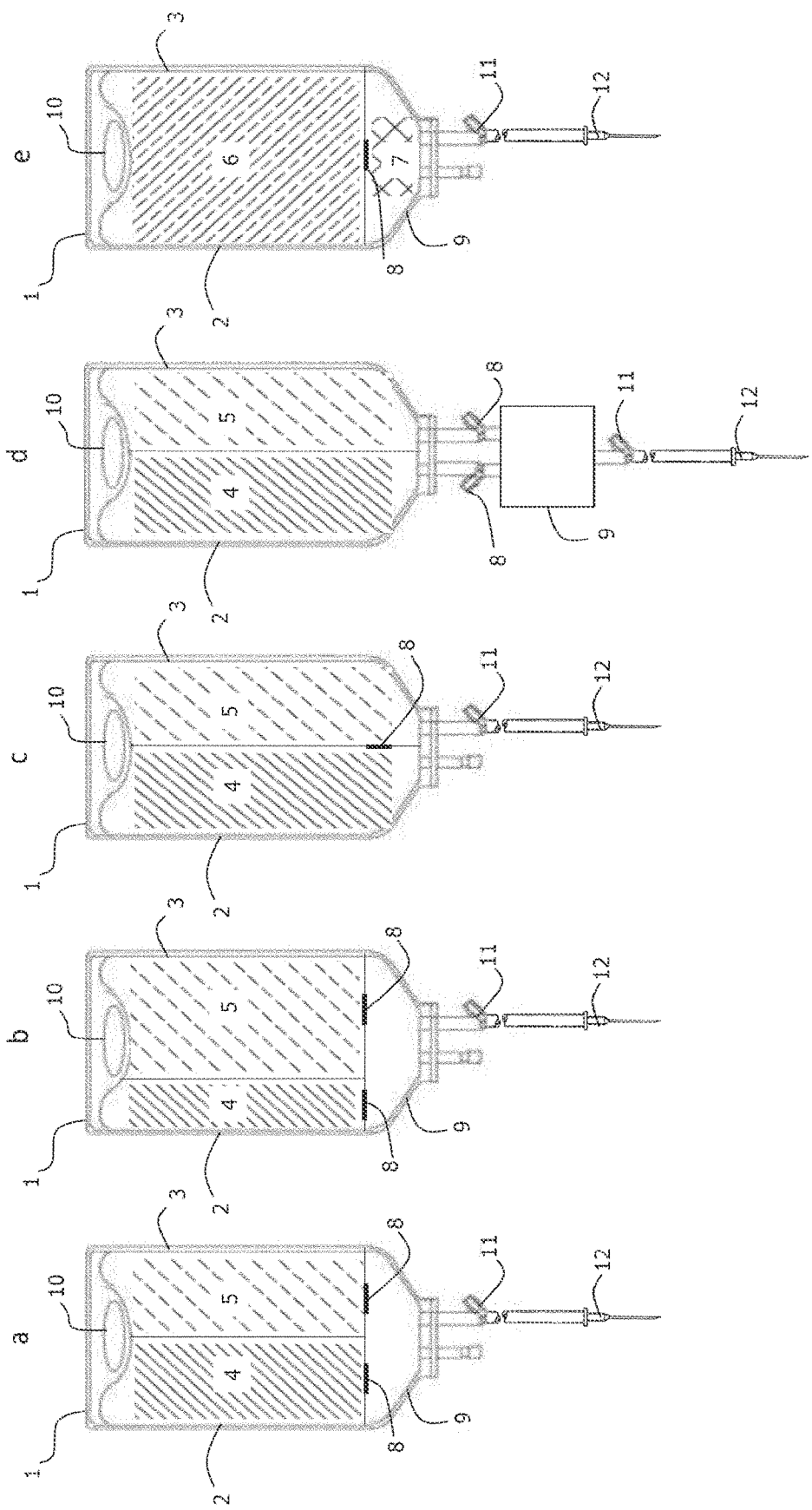

AQUEOUS FORMULATION COMPRISING PARACETAMOL AND IBUPROFEN

INCORPORATION BY REFERENCE TO ANY PRIORITY APPLICATIONS

Any and all applications for which priority claims are identified in the application data sheet, or any correction thereto, are hereby incorporated by reference, including the claim that this application is a continuation of U.S. application Ser. No. 17/502,899, filed Oct. 15, 2021, now U.S. Pat. No. 11,389,416, which is a continuation of U.S. application Ser. No. 16/424,274, filed May 28, 2019, now U.S. Pat. No. 11,213,498, which is a divisional of U.S. application Ser. No. 15/326,958, filed Jan. 17, 2017, now U.S. Pat. No. 11,219,609, which is the U.S. National Phase of International Application No. PCT/EP2015/066466, filed Jul. 17, 2015, designating the U.S. and published in English as WO 2016/009067 on Jan. 21, 2016, which claims the benefit of International Application No. PCT/EP2014/065544, filed Jul. 18, 2014 and published in English as WO 2016/008546 on Jan. 21, 2016.

BACKGROUND OF THE INVENTION

Field of the Invention

The present invention relates to a method for the preparation of a stable aqueous formulation combining ibuprofen and paracetamol, to compositions obtained using the method, and to their use as a medicine especially for intravenous injection or infusion.

The invention is particularly useful for use in hospitals where it is desirable to have access to stable liquid pharmaceutical formulations combining ibuprofen with paracetamol for administration by injection, in particular for intravenous injection or infusion.

Description of the Related Art

Ibuprofen is a known non-steroidal anti-inflammatory drug that possesses analgesic and antipyretic activities. Its chemical name is 2-(p-isobutylphenyl)propionic acid. It is indicated in the treatment for relief of signs and symptoms of rheumatoid arthritis and osteoarthritis, mild to moderate pain and treatment of primary dysmenorrhea.

Ibuprofen is very poorly soluble in water. Consequently dosage forms such as oral or injectable liquids have been difficult to develop. An approach followed to improve water solubility has been the use of water-soluble complexes and the preparation of an ibuprofen salt such as sodium or with an amino acid.

Paracetamol, also known as acetaminophen, is a known non-opiate, non-salicylate analgesic and antipyretic drug. Its chemical name is N-(4-hydroxyphenyl)acetamide. It provides temporary relief of minor aches and pains with heartburn or acid ingestion and upset stomach associated with these symptoms.

It is known that paracetamol in aqueous solution is liable to undergo hydrolysis. The formation of p-aminophenol following hydrolysis of paracetamol which itself can degrade into quinoncimine is for instance described in the publication of J. E. Fairbrother, "Acetaminophen" in Analytical Profiles of Drug Substances, 1974, vol. 3, pages 1-109. The rate of degradation of paracetamol increases with increasing temperature and light. This rate is minimal at a pH in the region of 6 (K. T. Koshy et al., 1961, J. Pharm. Sci. 50, pages 116-118). Paracetamol is also known as being susceptible to oxidation. Its stability in aqueous solutions therefor requires the use of antioxidants and/or the removal of oxygen from the solution. This poses extra constrains on the development of a formulation for intravenous injection on account of the toxicity of some antioxidants and/or complexity to remove oxygen which dissolves easily in water. Depending on the technique used the removal of oxygen may require a considerable amount of time. Another disadvantage is that oxidation products lead to the formation of coloured compounds, making the aqueous solution unsuitable for therapeutic applications.

Use of ibuprofen alone is associated with a number of side effects such as rash, ringing in the ears, headaches, dizziness, drowsiness, abdominal pain, nausea, diarrhoea, constipation and heartburn. The side effects may lead to patient discomfort and may result in poor medication follow up. A known approach is the combination with other active principles complementary to ibuprofen, preferably allowing a lower dose of ibuprofen.

There is a demand in the field for products that combine ibuprofen and paracetamol, especially in a form suitable for intravenous injection.

The pH of existing formulations in the market of ibuprofen alone is about 7. Ibuprofen sodium formulations commonly have a pH ranging from 7.0 to 7.4 and are buffered. Ibuprofen lysate formulations have a pH ranging from 6.8 to 7.1. The pH of existing paracetamol formulations in the market is about 5.5 to 6.0. The pH of 7 avoids precipitation of ibuprofen and the pH of 5.5 to 6.0 is advantageous for paracetamol as hydrolytic degradation of paracetamol is minimal at this pH. At pH 7 degradation of paracetamol is significant and at pH 5.5 to 6.0 ibuprofen precipitates.

It is the aim of the present invention to provide a combination product of ibuprofen and paracetamol that solves at least one of the problems described above. In particular the invention aims to provide a combination product in aqueous form suitable for intravenous injection. It is a further object of the invention to provide a method for the preparation of the ibuprofen/paracetamol combination.

SUMMARY OF THE INVENTION

The current invention provides a solution for at least one of the above mentioned problems by providing a composition combining ibuprofen and paracetamol with improved compatibility.

In a first aspect, the present invention provides in a process for manufacturing an aqueous composition comprising ibuprofen and paracetamol in combination, comprising the steps of:
 a) providing an aqueous solvent of pH 6.0-8.0, preferably 6.2-7.5, more preferably 6.3-7.3,
 b) dissolving in said aqueous solvent ibuprofen and paracetamol,
 c) if required adjusting the pH to 6.3-7.3,
 d) thereby obtaining said aqueous composition comprising ibuprofen and paracetamol in combination at pH 6.3-7.3.

More specifically, a process for manufacturing an aqueous composition comprising ibuprofen and paracetamol in combination, comprising in order the steps of: providing an aqueous solvent of pH 6.0-8.0, preferably 6.2-7.5, more preferably 6.3-7.3, and dissolving in said aqueous solvent 2.8 to 3.2 mg ibuprofen and 9.8 to 10.2 mg paracetamol expressed per ml of said composition. The pH of the final composition obtained should be between pH 6.3-7.3. Thus, if required, the pH is adjusted.

This method has the advantages that conditions are used which at the same time overcome poor ibuprofen solubility and paracetamol sensitivity to degradation. The resulting product has long term storage stability.

In a second aspect, the present invention provides aqueous compositions, preferably obtained by a method of the invention.

More specifically, the invention provides an aqueous composition, comprising ibuprofen and paracetamol, wherein the pH of said composition is 6.3 to 7.3.

Products according to an embodiment of the invention are characterized in that they provide a stable combination of ibuprofen and paracetamol at a physiologically acceptable pH.

In a third aspect, the present invention provides medical uses of the compositions according to the invention. Products according to the invention can be advantageously used to administer at the same time ibuprofen and paracetamol. The problem of managing the two drugs separately is overcome.

In a forth aspect, the invention provides in an device for delivery of an aqueous solution of ibuprofen and paracetamol at pH 6.3-7.3 in accordance with the invention.

The invention thereto provides a device (1) comprising a composition according to an embodiment of the invention for delivering said aqueous composition by means of injection or infusion. This device can be a syringe or infusion bag.

This device can be ready for use, i.e. comprising said aqueous solution of ibuprofen and paracetamol at pH 6.3-7.3. It can also be equipped for mixing of separate components of the solution prior to administration.

In a preferred embodiment said device comprises
at least a first and a second reservoir (2,3), wherein ibuprofen is comprised in a first reservoir (2) and paracetamol is comprised in a second reservoir (3), and
a mixing zone (9) for combining said paracetamol and said ibuprofen prior to delivery,
characterized in that, said combination is a composition according to an embodiment of the invention.

BRIEF DESCRIPTION OF THE DRAWINGS

FIG. 1 depicts several different embodiments a-e of an infusion bag 1, as examples of delivery devices according to the invention.

DETAILED DESCRIPTION OF THE PREFERRED EMBODIMENT

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints. All percentages are to be understood as percentage by weight and are abbreviated as "% wt", unless otherwise defined or unless a different meaning is obvious to the person skilled in the art from its use and in the context wherein it is used.

In a first aspect, the present invention provides in a process for manufacturing an aqueous composition comprising ibuprofen and paracetamol in combination, comprising the steps of:
a) providing an aqueous solvent of pH 6.0-8.0, preferably 6.3-7.3,
b) dissolving in said aqueous solvent ibuprofen and paracetamol,
c) if required adjusting the pH to 6.3-7.3,
d) thereby obtaining said aqueous composition comprising ibuprofen and paracetamol in combination and pH 6.3-7.3.

More specifically, a method for the production of an aqueous composition comprising ibuprofen and paracetamol in combination according to an embodiment of the invention, comprises in prescribed order the steps of: providing an aqueous solvent of pH 6.0-8.0, preferably pH 6.3-7.3, and dissolving in said aqueous solvent 2.8 to 3.2 mg ibuprofen and 9.8 to 10.2 mg paracetamol expressed per ml of said composition.

The invention also relates to a liquid formulation obtainable by a method of the invention. The invention also relates to a liquid formulation obtained by a method of the invention.

With the term "aqueous" is meant, comprising water. Preferably the aqueous solvent is water and more preferably a saline solution.

Preferably, the ibuprofen and paracetamol are dissolved in the aqueous solvent under mechanical agitation e.g. stirring. Ibuprofen is preferably used in the form of ibuprofen sodium. The amount of ibuprofen in the combination product is 2.8 to 3.2 mg per ml of the composition; preferably the amount is 3.0 mg/ml. Preferably ibuprofen sodium is used. For an amount of 3.0 mg ibuprofen/ml 3.85 mg ibuprofen sodium is used.

The amount of paracetamol in the combination product is 9.8 to 10.2 mg; preferably 10.0 mg/ml.

The aqueous solvent to which the active ingredients are added is characterized by a pH of 6.0-8.0, preferably 6.2-7.5, preferably 6.3 to 7.3. In a more preferred embodiment, the aqueous solvent has a pH of 6.4-6.6. In a more preferred embodiment, the final composition has a pH of 6.4-6.6. With "final composition", the composition is meant that will be filled into receptacles and is stored. It was found advantageous to start at the low end of the pH range. The final product has a pH on storage that remains stable or may evolve within the specified range (6.3-7.3).

The pH range at the same time avoids the precipitation of ibuprofen and degradation of paracetamol.

The pH may be adjusted to a desired level prior to admixing using a pH adjuster such as NaOH or HCl.

The pH of the solution may be buffered. Suitable buffering agents may include one or more of citric acid, sodium citrate, sodium phosphate, potassium citrate, and the like. Preferably the buffering agent is disodium phosphate.

In a preferred embodiment the aqueous solvent has a dissolved oxygen content below 2 ppm.

An oxygen content of maximum 2 ppm is a favourable level for avoiding degradation of paracetamol in the presence of ibuprofen, in the present method and compositions obtained thereof.

In a preferred embodiment the oxygen content of the aqueous solution is below 5 ppm, preferably below 2 ppm, more preferably below 1 ppm, even more preferably below 0.5 ppm, most preferably below 0.2 ppm.

The dissolved oxygen content can be measured by techniques known to a skilled person. The initial or residual dissolved oxygen content can be measured with the aid of an oxygen meter operating according to the Clark principle giving the value of the oxygen content in mg/l. The scale is calibrated between a point zero (reducing solution) and the content at oxygen saturation of distilled water, taking into account the temperature of the medium and the atmospheric pressure. The oxygen content is calculated using a chart as a function of the temperature and the pressure.

In a preferred embodiment of a process of the invention the reduced dissolved oxygen content is obtained using an aqueous solvent having a temperature, as from the outset, of between 65° C. and 99° C., preferably between 80° C. and 98° C. In an embodiment, the invention relates to a method as defined herein, wherein the aqueous solvent has, as from the outset, a temperature between 85° C. and 97° C. or between 90° C. and 95° C.

A preferred process comprises admixing of the active principles to the aqueous solvent that has a raised temperature. Advantageously, the aqueous solvent is not cooled prior to admixture of the active principle, which constitutes not only a gain in the preparation time of the formulation as there is no need to use heat exchangers to cool the aqueous solvent, but also permits to obtain a suitable oxygen concentration. Addition of the oxygen sensitive paracetamol and anti-oxidant to a medium with lowered oxygen content, as opposed to deoxygenation of the solution already containing these ingredients, has the advantage that the detrimental effects of oxygen are kept minimal. The anti-oxidant is not prematurely consumed as remains available to provide long term storage stability.

In another preferred embodiment of a process of the invention the reduced oxygen content is obtained by bubbling of an inert gas through said solvent. The gas that is bubbled into the solution to drive out oxygen may be nitrogen, argon or xenon. Preferred is nitrogen. Most preferred is nitrogen with low oxygen content.

In another embodiment of a process of the invention the reduced oxygen content is obtained using vacuum. Vacuum may be obtained using an appropriate vacuum pump such as a vane pump.

Techniques for reduction of the oxygen content in the formulation, such as the warm water, bubbling and/or vacuum method as described above, may be combined.

In a preferred embodiment, the solution before filling in a receptacle, is topped up with an inert gas, such as nitrogen, argon or xenon. Preferred is argon. The use of argon is advantageous as it is heavier than air and is believed to provide a protective layer on top of the solution.

In a preferred embodiment of a process of the invention, the pH of the aqueous solvent in step a) is 6.3 to 6.5. Starting the process at a pH of 6.4±0.1 has the advantage that the resulting composition has a longer storage stability.

In a preferred embodiment, solutions prepared with a process of the invention, with pH of 6.4+/−0.1, have a storage stability of at least 6 months, preferably 12 months, more preferably 18 months, most preferably 18 months.

In another preferred embodiment, solutions prepared with a process of the invention, with pH of 6.3-6.6 at the time of preparation ($t_0$), have a storage stability of at least 6 months ($t_6$), preferably at least 8 months ($t_8$), more preferably at least 10 months ($t_{10}$), most preferably at least 12 months ($t_{12}$).

In a preferred embodiment of a process and composition of the invention, an anti-oxidant is added to the aqueous composition. Anti-oxidants for use in the invention are preferably selected from the list of a sulphite, or sulphite derivative, a thiolic substance such as, for example, cysteine, acetylcysteine, dithiothreitol or alpha-thioglycerol, thiomalic acid, thioglycerol, methionine; a hydroxylated substance such as ascorbic acid, iso-ascorbic acid, mannitol, sorbitol, an ethylenically unsaturated substance such as sorbic acid, undecylenic acid or fumaric acid or a hydroxy polycarboxylic acid, or a reducing sugar such as trehalulose, maltulose or isomaltulose. In a preferred embodiment the anti-oxidant is selected from a cysteine and acetyl cysteine. Cysteine is preferably cysteine hydrochloride. The acetyl cysteine or cysteine hydrochloride is preferably the monohydrate. By the term "(acetyl)cysteine" as used herein, is meant acetylcysteine and/or cysteine. Acetyl cysteine or cysteine as anti-oxidant suppresses the generation of unknown degradation products of paracetamol by oxidation. In spite of the risk that their use will provide yellow solutions, they are preferred as they can reduce the risk of paracetamol toxicity.

In case the warm water technique is used, the temperature of the composition is lowered to 40° C. or lower prior to addition of cysteine or acetyl cysteine. The cooling may be under mechanical agitation e.g. stirring. The anti-oxidant is added at a temperature of at most 40° C. to avoid degradation of the acetyl cysteine or cysteine at higher temperatures. The aqueous solution comprising ibuprofen and paracetamol is then cooled to a temperature of at most 40° C., preferably to 39° C. or 38° C., 37° C., 36° C. or 35° C., prior to the addition of acetyl cysteine or cysteine. Preferably the addition of cysteine or acetyl cysteine to said aqueous solvent does not change said pH outside of 6.3 and 7.3. In a preferred embodiment, the aqueous composition has a pH of 6.3 to 7.3 prior to and after addition of the anti-oxidant. Preferably the pH of the final product is around 6.6.

In a preferred embodiment of a process and composition of the invention the aqueous solvent further comprises an isotonic agent. Use of an isotonic agent has the advantage that an osmotic pressure is created in the region of that of physiological saline. The isotonic agent herein may be a polyol, a sugar, a linear or cyclic glucitol having from 2 to 10 carbon atoms selected from mannitol, sorbitol, inositol, glucose and glycerol. A preferred isotonic agent is mannitol.

The mass ratio (w/w) of the isotonic agent to paracetamol, for instance mannitol:paracetamol, is preferably 2 to 6:1, more preferably 3 to 5:1, most preferably around 4:1. Preferably the isotonic agent is added to the aqueous solution, preferably water, prior to the addition of ibuprofen and paracetamol.

In a preferred embodiment, the pH adjusters used in a method according to the invention, are sodium hydroxide-disodium phosphate salt and acetyl cysteine or cysteine.

In a preferred embodiment the final pH of the formulation is from 6.3 to 7.3. Preferably the final pH is 6.4 to 6.9, more preferably 6.5 to 6.8. In a preferred embodiment of a process of the invention the aqueous composition obtained has a pH around 6.6. Preferably the pH is 6.3 to 7.3 after a shelf-life of at least six months.

After the additions are complete, the reaction vessel is closed, and the air remaining in the upper side of the vessel is compressed by an inert gas such nitrogen, introduced from the upper side of the vessel. Preferably the pressure is at 1-1.5 bar. Following the introduction of inert gas, stirring ensues.

Preferably, the mass ratio (w/w) of cysteine hydrochloride to paracetamol is 0.010 to 0.040:1, preferably 0.020 to 0.030:1, preferably 0.025:1.

Preferably, the mass ratio (w/w) of acetyl cysteine or cysteine hydrochloride to ibuprofen is 0.20 to 0.40:1, preferably 0.10 to 0.20:1, preferably 0.08:1.

For example, in a formulation and method as defined herein, (acetyl)cysteine hydrochloride may be present in the final formulation in an amount preferably between 0.015% and 0.05%, preferably around 0.025% (w/v).

The solution obtained may be filtered, for example in a filtration unit.

As during compounding, oxygen contact or oxygen ingress into the aqueous solution during filling/packaging and/or storage is preferably avoided.

Preferably the containers, such as vials, for receipt of the paracetamol-ibuprofen solution are washed with warm water prior to filling. In particular, the containers may be washed with water for injection at a temperature of 75° C.-100° C. This water has a low dissolved oxygen content. It is particularly suitable to take up oxygen from the container and reduced its oxygen content.

In a subsequent step, the washed containers may be dried. Preferably drying is carried out with dry air. Dry air with low moisture content, again minimizes re-uptake of oxygen by the packaging and later on by the paracetamol-ibuprofen solution.

After drying the washed and/or dried containers may be rinsed with nitrogen. Preferably nitrogen low in oxygen is used.

Following the pre-treatment of the containers, said containers are filled with the ibuprofen/paracetamol solution.

The compounding procedure preferably provides an aqueous ibuprofen/paracetamol solution prior to filling/packaging with a dissolved oxygen content of below 2.0 ppm, more preferably below 1.0 ppm, even more preferably below 0.8 ppm, most preferably below 0.5 ppm; typically around 0.4 ppm.

In a preferred embodiment, a paracetamol-ibuprofen solution prepared according to a method of the invention has less than or equal to 0.8 ppm dissolved oxygen during filing.

Preferably the containers are sealed under vacuum; preferably said vacuum is between 450 mbar and around 1 bar.

The containers are then sealed, for instance by adding a stopper, sealing under vacuum and providing a crimping cap covering the stopper.

These bottles can subsequently be heat-sterilised, for instance for 15 minutes at 121° C.

In a preferred embodiment, a method according to the invention further comprises in specified order the steps of:
  ashing said containers with water for injection at a temperature of 75° C.-100° C.,
  drying said washed containers with dried air, rinsing said washed containers with nitrogen,
  filling said nitrogen washed container with the ibuprofen/paracetamol aqueous solution,
  sealing said container under vacuum, preferably between 450 mbar and around 1 bar.

In a more preferred embodiment, said vacuum sealed product container comprises a stopper made of an elastic material covered by a crimping cap.

In a preferred embodiment said elastic material of the stopper is rubber, preferably a butyl rubber or halo butyl rubber. These rubber types have a low oxygen transmission coefficient. Preferably the stopper is sealed by an aluminium crimping caps. Preferably said vial is closed with a (halo) butyl rubber stopper, preferably bromobutyl rubber, and sealed by an aluminium caps.

Preferably the container used to obtain a product according to an embodiment of the invention is a vial; preferably a colourless type II glass Eur. Ph. 3.2.1 vial.

In a preferred embodiment according to the invention the closed product container has reduced pressure inside. Preferably the pressure is reduced to allow the addition of solvent for injection to the closed system, e.g. by means of penetrating the closure with a needle. Preferably the reduced pressure is between 450 mbar and around 1 bar.

In a preferred embodiment the container comprises a vial with a blow back inside of the flange. The blow back improves the fit of the stopper and avoids that the stopper pops out of the vial. The flange of the vial and the dimensions of the stopper are chosen in a way to guarantee a good fit of the stopper during stoppering and sealing. It is preferred to have a blow back with dimensions in size to provide sufficient sealing surface between the vial and the stopper in order to keep a vacuum in the vial as long as possible.

Preferably the container/closure system has a blow back; particularly when applying reduced pressure. In comparison to systems having no blow back, blow back systems are very tight and the risk of influx of air and thus oxidation can be reduced.

A formulation according to an embodiment of the invention can generally be prepared as follows. First, exact quantities of the formulation of isotonic agent (mannitol), ibuprofen sodium and hydrochloric acid in an amount to obtain a pH of 6.3-7.3 are added to a reaction vessel. Optionally one or more other water-miscible solvent(s), and/or surfactants may be present. Then, as solvent, water for injections is provided at a temperature of between 65° C. and 98° C. The reaction vessel is closed and the air remaining in the upper side of the vessel is compressed by 0.22 µm filtered nitrogen introduction from the upper side of the vessel. Then components are dissolved by stirring. After, stirring is stopped the reaction vessel is quickly opened and paracetamol is quickly added. The procedure is at this point carried out without mixing to reduce the introduction of air. Then the reaction vessel is closed. Air is hardly soluble in water when it is at a temperature of more than 60° C.

Remaining air in the upper side of the vessel is compressed by 0.22 µm filtered nitrogen from the upper side, preferably at 1-1.5 bar, then stirring ensues. The solution is cooled to a temperature of at most 40° C. Once cooled, reaction vessel is quickly opened and exact quantities of sodium hydroxide and disodium phosphate of the formulation, for obtaining a pH 6.3-7.3, are quickly added and reaction vessel is closed. Remaining air in the upper side of the vessel is compressed by 0.22 µm filtered nitrogen from the upper side, preferably at 1-1.5 bar, stirring ensues. The reaction vessel is quickly opened and cysteine or acetyl cysteine is quickly added and the reaction vessel is again closed. The air remaining in the upper side of the vessel is compressed by 0.22 µm filtered nitrogen introduced from the upper side, preferably at 1-1.5 bar, then stirring ensues. The nitrogen used is filtered prior to its introduction with a 0.22 µm filter.

In a second aspect the present invention provides an aqueous composition, comprising ibuprofen and paracetamol, wherein the pH of said composition is 6.3 to 7.3.

More specifically, an aqueous composition comprising 2.8 to 3.2 mg ibuprofen, 9.8 to 10.2 mg paracetamol and cysteine expressed per ml of said composition, preferably prepared according to the method previously described, characterized in that, the pH of said composition is 6.3 to 7.3.

The present inventor has found that the indicated pH range unexpectedly allows the combination of ibuprofen and paracetamol in aqueous solution thereby at the same time reducing ibuprofen precipitation and paracetamol degradation.

Preferably the aqueous solvent comprises water and an isotonic agent. In a more preferred embodiment said isotonic agent is mannitol.

More pharmaceutically acceptable excipients may be present. However, in a preferred embodiment there are no additional excipients present.

Preferably the aqueous solution has an osmolality of between 285-320 mOsmoUl as determined by point depression according to USP 788.

In a preferred embodiment said composition has a storage stability of at least 6 months, preferably at least 9 months, more preferably at least 12 months, most preferably 24 months, based on the paracetamol/ibuprofen content as measured by HPLC in accordance with European Pharmacopeia 2.2.29 and USP 621.

In a preferred embodiment, the (acetyl)cysteine amount in the composition at the completion of its preparation is at least 80%, preferably at least 85%, most preferably at least 90%, of the initial amount added.

In a preferred embodiment, the (acetyl)cysteine hydrochloride content is at least 40% of the initial amount added, preferably at least 50%, preferably at least 75%, during the shelf-life of the ibuprofen/paracetamol solution. A low consumption of (acetyl)cysteine is indicative of a low exposure to oxygen during the period of storage.

In a further embodiment said composition is for use as a medicament. Especially important for its suitability in the pharmaceutical and medical field is the pH of the composition.

In a more preferred embodiment said composition is for use in the treatment of pain and/or of inflammation.

Its pH makes the composition particularly suitable for administration by intravenous injection. In a most preferred embodiment said composition is for administration by intravenous injection.

The solutions thus obtained may be distributed into ready-to-use hermetically stoppered or sealed, bags, pouches or bottles.

In a third aspect the invention provides in a device comprising a composition according to an embodiment of the invention for delivering said aqueous composition by means of injection or infusion.

In a preferred embodiment, said device comprises
at least a first and a second reservoir, wherein ibuprofen is comprised in a first reservoir and paracetamol is comprised in a second reservoir, and
a mixing zone for combining said paracetamol and said ibuprofen prior to delivery,
characterized in that, said combination is a composition according to an embodiment of the invention.

In a preferred embodiment, said first and second reservoir are separated from each other by temporary separation means. Upon connection of the reservoirs by removal or opening of the separation means, the reservoirs are used as a mixing zone.

This has the advantage that the different components can be formulated in the for each component most stable storage conditions. This allows storing the amount of paracetamol separately at its most favourable pH from the amount of ibuprofen at its most favourable pH. Alternatively, it allows storage of the aqueous solvent separately from the amount of paracetamol or ibuprofen. Just before administration of the composition to a patient, the temporary sealing means are removed or opened and the different components can be mixed together.

The term "device" refers to a medical device for parenteral administration of a composition, preferably intravenous administration of a liquid composition.

In a preferred embodiment, the injection device is in the form of a syringe.

This has the advantage that a medical practitioner knows how to use said injection device.

In a preferred embodiment, the injection device is in the form of an infusion bag.

This has the advantage that larger volumes can be administered to the patient, and hence larger quantities of ibuprofen and paracetamol can be administered than with a syringe. The speed of administration can be controlled so that administration over a long period of time can be achieved.

The term "temporary sealing means" refers to means to prevent a fluid to flow from one reservoir to another, or to prevent a fluid to flow from a reservoir to the mixing zone. These means can be broken, opened or removed in a way fluid can flow from said reservoirs. The sealing means can be broken, opened or removed reversibly or permanently. The sealing means can be a tap, a valve, a breakable protrusion or a weakened section in the separation between the reservoirs or mixing zone.

In a preferred embodiment, the aqueous solvent is divided over the different reservoirs and can have a different pH in each reservoir.

In a preferred embodiment, the pH of solutions in the said at least two reservoirs is different, preferably 1.0 to 2.0 pH units difference. This corresponds for instance, to a paracetamol solution with pH 5.8-6.0 in one reservoir, and an ibuprofen solution of pH 7.0-8.0 in another reservoir.

This has the advantage that one reservoir can hold ibuprofen at its most stable pH and another reservoir can hold paracetamol at its most stable pH.

In a preferred embodiment, the injection device is comprising in a first reservoir said ibuprofen solubilised in water at pH 7.0-8.0.

This has the advantage that ibuprofen is already solubilized so that upon administration no time needs to be spend solubilizing the amount of ibuprofen. The pH at which the ibuprofen is solubilized is the pH at which an ibuprofen solution is most stable, meaning the smallest amount of decomposition of ibuprofen occurs. This allows the ibuprofen solution to be stored preferably at least one year, more preferably at least 2 years.

In a preferred embodiment, the injection device is comprising in a second reservoir said paracetamol solubilised in aqueous solvent of pH of 5.5 to 6.0.

This has the advantage that paracetamol is already solubilized so that upon administration no time needs to be spend solubilizing the amount of paracetamol. The pH at which the paracetamol is solubilized is the pH at which a paracetamol solution is most stable, meaning the smallest amount of decomposition of paracetamol occurs. This allows the paracetamol solution to be stored preferably at least six months, more preferably one year, most preferably at least 2 years.

In a preferred embodiment, the injection device comprises a mixing zone, temporarily or permanently, fluidly separated from said reservoirs. The mixing zone is preferably fluidly separated from said reservoirs by temporary sealing means.

This has the advantage that only in the mixing zone conditions are unfavourable for long term storage. The composition will only be present in the mixing zone for a short time before administration. This time is too short to for one of the components of the composition to decompose.

In a more preferred embodiment, one of the reservoirs or both of the reservoirs become the mixing zone after the removal of the temporary sealing means.

This has the advantage that no empty volumes need to be provided. The empty volumes have the disadvantage that these can be filled with air, and precaution needs to be taken that the air does not get into the bloodstream upon administration.

The pH in the mixing zone is 6.3 to 7.3. It has been shown by the inventor that this is the optimal pH range for having both ibuprofen and paracetamol in solution in terms of stability.

In a preferred embodiment, a device is foreseen with an injection means and the injection means is a hypodermic needle or a connector to a hypodermic needle, a catheter or a drip.

This has the advantage that the injection device can be integrated in common medical practice.

In a further aspect of the invention, the composition is provided in a double chambered device, preferably an injection device.

In a preferred embodiment said injection device is provided with a composition according to an embodiment of the invention. Preferably it is comprising a first and a second reservoir, wherein ibuprofen in an amount for providing 2.8 to 3.2 mg ibuprofen expressed per ml of said composition is comprised in one of the reservoirs and paracetamol in amount for providing 9.8 to 10.2 mg paracetamol expressed per ml of said composition is comprised in the other reservoir, characterized in that, the pH of said composition when the content of both reservoirs is mixed is from 6.3 to 7.3.

In a preferred embodiment said injection device is provided with a composition according to an embodiment of the invention comprising a first and a second reservoir, wherein 2.8 to 3.2 mg ibuprofen expressed per ml of said composition is comprised in one of the reservoirs and 9.8 to 10.2 mg paracetamol expressed per ml of said composition is comprised in the other reservoir, characterized in that, the pH of said composition when the content of both reservoirs is mixed is from 6.3 to 7.3.

In a preferred embodiment the injection device, comprises a first and a second reservoir, which first reservoir has a first open end through which the second reservoir can be mounted sliding in the first reservoir, which first reservoir has a second end located opposite the first end and on which an injection needle can be arranged, which second reservoir comprises a base surface which is fitted with an outlet, wherein at the outlet is arranged a protrusion which in mounted state of the injection device extends from the base surface in the direction of the second end, which protrusion is arranged breakably on the base surface of the second reservoir, such that when the protrusion reaches the second end it breaks away to open the outlet of the second reservoir.

Such an injection device is characterised in that a protrusion is mounted at the outlet and in the mounted state of the injection device extends from the base surface towards the second end, which protrusion is mounted breakably on the base surface of second reservoir, such that when the protrusion reaches the second end, it breaks off to open the outlet of the second reservoir. Because the protrusion is arranged on the base surface of the second reservoir and breaks away on reaching the second end, it does not form an obstacle for the outflow of the medication from the first reservoir. The evacuation of the first reservoir is therefore optimal. Because in addition the protrusion is arranged at the outlet of the second reservoir in the base surface, this can take place at the same time as the production of the injection device without extra steps on injection moulding of the second reservoir. The injection device is cheap to produce.

Suitable devices, in particular syringes, for use in the present invention are for instance described in BE1020614.

The invention is described in greater detail in the examples below, which are given as non-limiting illustrations. In these examples, the temperature is room temperature or is expressed in degrees Celsius, and the pressure is atmospheric pressure. The water and all the reagents used are of injectable grade.

Moreover, all the examples form an integral part of the invention, as does any characteristic of the description including the examples, which appears to be novel with respect to any prior art, in the form of a general characteristic rather than of a particular characteristic of the example.

Examples

In the following, examples are intended to further clarify the present invention, and are nowhere intended to limit the scope of the present invention.

1. Preparation of Liquid Pharmaceutical Formulations According to the Present Invention Formulations were prepared by admixing isotonic agent (mannitol) ibuprofen, hydrochloric acid, water for injections, paracetamol and acetyl cysteine or cysteine, and pH is at 6.3-7.3 by hydrochloric acid, sodium hydroxide and disodium phosphate. The preparation of the composition was followed by filtration and filling of glass vials or bottles. The filtration of the solution took place at a temperature below 40° C. These receptacles were sterilized for 15 minutes at 121° C.

The relevant manufacturing steps are performed quickly and without any unnecessary interruption in order to avoid incorporation of air in the compounding vessel and to keep the solution at the required temperatures i.e. between 65° C. and 98° C. for the admixing steps before acetyl cysteine or cysteine are added; and below 40° C. for the acetyl cysteine or cysteine addition part.

The air inside the reaction vessel was compressed from the upper side of the vessel by 0.22 μm filtered nitrogen pressure. The nitrogen pressure applied on the solution in the compounding vessel pushes the solution through the filter.

Finally, the filled vials were sterilized at 121° C. for 15 minutes.

TABLE 1

Formulation 1

| Name of ingredient | Unit formula 100 ml | Formula per 1 ml |
|---|---|---|
| Ibuprofen sodium | Equivalent to 300 mg ibuprofen | Equivalent to 3 mg ibuprofen |
| Paracetamol | 1.0 g | 10 mg |
| Mannitol | 3.2850 g | 32.850 mg |
| Hydrochloric acid | to pH = 6.6 | to pH = 6.6 |
| Cysteine hydrochloride monohydrate | 25.0 mg | 0.25 mg |
| Di sodium phosphate dihydrate | 13.0 mg | 0.13 mg |
| Sodium hydroxide | to pH = 6.6 | to pH = 6.6 |
| Water For Injection | q.s. ad 100.0 ml | q.s. ad 1.0 ml |
| Nitrogen Low Oxygen | q.s. | q.s. |

2. Preparation of an Alternative Liquid Pharmaceutical Formulation According to the Present Invention An alternative formulation was prepared according to the method described under Example 1.

TABLE 2

Formulation 2

| Name of ingredient | Unit formula 100 ml | Formula per 1 ml |
|---|---|---|
| Ibuprofen sodium | Equivalent to 300 mg ibuprofen | Equivalent to 3 mg ibuprofen |
| Paracetamol | 1.0 g | 10 mg |
| Mannitol | 3.2850 g | 32.850 mg |
| Hydrochloric acid 1M/Sodium hydroxide 1M | to pH = 6.4 | to pH = 6.4 |
| Cysteine hydrochloride monohydrate | 25.0 mg | 0.25 mg |
| Di sodium phosphate dihydrate | 15.0 mg | 0.15 mg |
| Water For Injection | q.s. ad 100.0 ml | q.s. ad 1.0 ml |
| Nitrogen Low Oxygen | q.s. | q.s. |

3. Storage Stability Data

An ibuprofen/paracetamol combination product was prepared as follows:

To a mixing tank were added mannitol, ibuprofen, hydrochloric acid 0.1 N for obtaining a pH of 6.3 to 7.3 and water for injections (WFI) at a temperature above 75° C. The quantity of hydrochloric acid to be added was calculated in advance and is such that the desired pH is maintained 6.3-7.3. The mixing vessel was closed and the air remaining in the upper side of the vessel was compressed by 0.22 μm filtered nitrogen introduced from the upper side, at 1-1.5 bar, followed by stirring.

The mixing vessel was quickly opened and paracetamol was quickly added without stirring. The mixing vessel was closed and the remaining air in the upper side of the vessel was compressed by 0.22 μm filtered nitrogen introduced from the upper side of the vessel, at 1-1.5 bar, followed by stirring.

The solution was cooled to a temperature below 40° C. The temperature reached, the mixing vessel was quickly opened and sodium hydroxide 0.1 N and disodium phosphate were quickly added without stirring. Mixing vessel was closed and the air remaining in the upper side of the vessel was compressed by 0.22 μm filtered nitrogen introduced from the upper side of the vessel, at 1-1.5 bar, followed by stirring.

The quantities of sodium hydroxide and disodium phosphate to be added were calculated in advance and are such that the desired pH is maintained at 6.3-7.3 after the addition of cysteine.

The mixing vessel was quickly opened and acetyl cysteine or cysteine was quickly added without stirring. The mixing vessel was closed and the air remaining in the upper side of the vessel was compressed by 0.22 μm filtered nitrogen introduced from the upper side of the vessel, at 1-1.5 bar, followed by stirring.

Samples were stored and analysed after set time-intervals. The results for the solutions of pH 6.6 stored at a temperature of 25+/−2° C. at a relative humidity of 40+/−5% are summarized in Table 8. Those of pH 7.0 stored at a temperature of 25+/−2° C. at a relative humidity of 40+/−5% are provided in Table 9. Further results from a storage stability test on samples prepared as previously described, are provided in Table 10. These samples were kept at a temperature of 25+/−2° C. and a relative humidity of 40+/−5%. Those of pH 6.4 stored at a temperature of 25+/−2° C. at a relative humidity of 60+/−5% are provided in Table 11.

A series of analysis was performed on the sample. The appearance of a solution was determined by visual inspection according to USP 641, pH values were determined using potentiometry using USP 791, coloration was determined following Eur. Ph 2.2.2 point depression USP 785, sub visible particles were assessed using a light obscuration particle count method USP 788, cysteine. $HCl* H_2O$, ibuprofen and acetaminophen were identified using liquid chromatography USP 621. Acetaminophen content was determined by HPLC, Eur. Ph. 2.2.29, 0049. Ibuprofen content and amount of cysteine $HCl*H_2O$ are determined by liquid chromatography USP 621. Acetaminophen impurities were determined using Eur. Ph 2.2.29, 0049. Ibuprofen impurities were determined using Eur. Ph 2.2.29.

From the data in both tables it can be seen that a clear liquid solution is provided. The physical appearance is obtained even after twelve months of storage and more. The cysteine content remains high and essentially stable over time. Impurity levels are very low for both paracetamol and ibuprofen, in spite of the pH considered disadvantages for the active principles when present alone.

The storage stability test results indicate that a product shelf-life of two years is feasible. It can be concluded that the invention provides stable ibuprofen/paracetamol combination products of pH 6.3-7.3.

4. Compatibility

To test the compatibility of ibuprofen and paracetamol in combination, the following experiment was performed.

The pH 8.80 of a solution of 3.85 mg/ml of sodium ibuprofen $2H_2O$, equivalent to 3 mg/ml of ibuprofen, in water is gradually decreased and the absence or presence of precipitation is observed as an indication of solubility/compatibility. The results are noted down and summarized in Table 3. Precipitation of ibuprofen is observed once pH is at 5.75. The Ibuprofen solutions were stored for 1 month at 25° C. They were again observed for signs of precipitation. The results are summarized in Table 4. Ibuprofen solutions at pH 6 showed precipitation, whereas in solutions of ibuprofen at pH 6.2, precipitation was absent.

TABLE 3

Dissolution of sodium ibuprofen 2H$_2$O alone in water

| pH | 3 | 4 | 5 | 5.5 | 5.8 | 6 | 6.2 | 6.4 | 6.6 | 6.8 | 7 | 7.5 |
|---|---|---|---|---|---|---|---|---|---|---|---|---|
| Dissolved | No | No | No | No | Yes | Yes | Yes | Yes | Yes | Yes | Yes | Yes |

TABLE 4

Dissolution of sodium ibuprofen 2H$_2$O in water after 1 month storage at 25° C.

| pH | 5.8 | 6 | 6.2 | 6.4 | 6.6 | 6.8 | 7 | 7.5 |
|---|---|---|---|---|---|---|---|---|
| Dissolution | No | No | Yes | Yes | Yes | Yes | Yes | Yes |

In a further experiment the dissolution of sodium ibuprofen 2H$_2$O was studied in combination with paracetamol at a concentration of 10 mg paracetamol per liter. The results at varying pH are summarized in Table 5. The results after one month of storage at 25° C. are provided in Table 6.

TABLE 5

Dissolution of sodium ibuprofen 2H$_2$O in the formulation 3 mg/ml Paracetamol 10 mg/ml Ibuprofen

| pH | 6.2 | 6.3 | 6.4 | 6.6 | 7 |
|---|---|---|---|---|---|
| Dissolved | Yes | Yes | Yes | Yes | Yes |

TABLE 6

Dissolution of sodium ibuprofen 2H$_2$O in the formulation Paracetamol-Ibuprofen-1 month

| pH | 6.2 | 6.3 | 6.4 | 6.6 | 7 |
|---|---|---|---|---|---|
| Dissolution | No | Yes | Yes | Yes | Yes |

TABLE 7

Dissolution of sodium ibuprofen 2H$_2$O in the formulation Paracetamol-Ibuprofen-6 months, 25° C.

| pH | 6.3 | 6.4 | 6.6 | 7 |
|---|---|---|---|---|
| Dissolution | Yes | Yes | Yes | Yes |

The amount of paracetamol was studied at varies points in time and for different pH's. Data showed that minimal degradation of paracetamol occurred at the pH range 6.3-7.3.

From the above it is concluded that the combination of ibuprofen and paracetamol is stable with a pH range of 6.3-7.3.

5. Injection Device

FIG. 1 depicts several different embodiments a-e, according to the invention of injection devices in the form of an infusion bag 1. FIG. 1a shows in infusion bag 1 according to an embodiment of the invention comprising a first reservoir 2 holding an amount of ibuprofen solubilised 4 in a part of the aqueous solvent. The infusion bag also comprises a second reservoir 3 holding an amount of paracetamol solubilised 5 in the rest of the aqueous solvent. The temporary sealing means 8 separate these reservoirs 2 and 3 from the mixing zone 9. The injection means 12 are connected to the mixing zone 9 and a flow regulator 11 is provided between said injection means 12 and said mixing zone 9. The infusion bag can be hung up by the fastening means 10. FIG. 1b, shows an infusion bag 1 according to an embodiment of the invention with a similar setup but with reservoirs 2 and 3 having different volumes. FIG. 1c shows an infusion bag 1 with no separate mixing zone, the mixing zone is formed by reservoirs 2 and 3 once the temporary sealing means 8 are removed. FIG. 1d shows an infusion bag 1 with a mixing zone 9 that is not housed in the infusion bag 1 itself. FIG. 1e shows an infusion bag 1 according to an embodiment of the invention. Reservoir 3 is holding an aqueous solvent 6 with a pH between 6.3 and 7.3 and reservoir 2 is holding an amount of ibuprofen and an amount of paracetamol 7 in dry conditions.

TABLE 8 storage stability date 3 mg/ml ibuprofen 10 mg/ml paracetamol with cysteine (pH 6.6, 25 +/− 2° C., 40 +/− 5% relative humidity)

| Analysis | Specification | 1 month | 2 months | 3 months | 6 months | 9 months | 12 months | 15 months | 18 months | 24 months |
|---|---|---|---|---|---|---|---|---|---|---|
| Appearance of solution | Clear liquid | clear liquid | clear liquid | clear liquid | clear liquid | clear liquid | clear liquid | clear liquid | clear liquid | clear liquid |
| pH value | To be determined | 6.66 | 6.66 | 6.69 | 6.70 | 6.75 | 6.72 | 6.79 | 6.81 | 6.83 |
| Coloration | ≤Y6 | <Y6 | <Y6 | <Y6 | <Y6 | <Y6 | <Y6 | <Y6 | <Y6 | <Y6 |
| Sub visible particles | ≥10 μm: ≤6000 p/vial | 3158 | 1020 | 3885 | 905 | 2582 | 4895 | N.R. | 1790 | 888 |
| | ≥25 μm: ≤600 p/vial | 50 | 5 | 20 | 38 | 47 | 65 | N.R. | 40 | 17 |
| Identification | | | | | | | | | | |
| Cysteine HCl*H$_2$O | Same retention time | Complies | Complies | Complies | Complies | Complies | Complies | Complies | Complies | Complies |

TABLE 8-continued storage stability date 3 mg/ml ibuprofen 10 mg/ml paracetamol with cysteine (pH 6.6, 25 +/− 2° C., 40 +/− 5% relative humidity)

| Analysis | Specification | 1 month | 2 months | 3 months | 6 months | 9 months | 12 months | 15 months | 18 months | 24 months |
|---|---|---|---|---|---|---|---|---|---|---|
| Ibuprofen | as standard | Complies | Complies | Complies | Complies | Complies | Complies | Complies | Complies | Complies |
| Acetaminophen | | Complies | Complies | Complies | Complies | Complies | Complies | Complies | Complies | Complies |
| Acetaminophen content (HPLC) | 95-105% | 104 | 104 | 104 | 101 | .99 | 101 | 103 | 104 | 103 |
| Ibuprofen content (HPLC) | 95-105% | 104 | 104 | 103 | 102 | 103 | 100 | 102 | 103 | 103 |
| Cysteine HCl*$H_2O$ (HPLC) | Min 60% | 89% | 86% | 87% | 90% | 87% | 85% | 90% | 72% | 84% |
| Impurities Acetaminophen | | | | | | | | | | |
| Impurity K (4-aminophenol) | <0.05% | 0.02 | 0.02 | 0.01 | 0.01 | 0.03 | 0.03 | 0.03 | 0.04 | 0.03 |
| Impurity F (4-nitrophenol) | <0.05% | 0.00 | 0.00 | 0.00 | 0.00 | 0.00 | 0.00 | 0.00 | 0.00 | 0.00 |
| Any other impurity | <0.10% | 0.01 | 0.01 | 0.01 | 0.01 | 0.02 | 0.03 | 0.02 | 0.03 | 0.01 |
| Total impurities | <0.2% | 0.0 | 0.0 | 0.0 | 0.0 | 0.0 | 0.1 | 0.0 | 0.1 | 0.0 |
| Impurities Ibuprofen | | | | | | | | | | |
| Impurity A | <0.1% | 0.0 | 0.0 | 0.0 | 0.0 | 0.0 | 0.0 | 0.00 | 0.00 | 0.00 |
| Impurity B | <0.2% | 0.0 | 0.0 | 0.0 | 0.0 | 0.0 | 0.0 | 0.00 | 0.00 | 0.00 |
| Any other impurity | <0.10% | 0.00 | 0.00 | 0.00 | 0.00 | 0.00 | 0.00 | 0.000 | 0.000 | 0.000 |
| Total impurities | <0.2% | 0.0 | 0.0 | 0.0 | 0.0 | 0.0 | 0.00 | 0.00 | 0.00 | 0.00 |

TABLE 9 storage stability data-3 mg/ml ibuprofen and 10 mg/ml paracetamol with cysteine (pH 7.0, 25 +/− 2° C., 40 +/− 5% relative humidity)

| Analysis | Specification | Method and Method No. | 1 month | 2 months | 3 months | 6 months |
|---|---|---|---|---|---|---|
| Appearance of solution | Clear liquid | Visual inspection.USP<641> | clear liquid | clear liquid | clear liquid | clear liquid |
| pH value | To be determined | Potentiometry.USP<791> | 7.02 | 6.99 | 7.00 | 7.00 |
| Coloration | ≤Y6 | Eur.Ph 2.2.2 | <Y6 | <Y6 | <Y6 | <Y6 |
| Sub visible particles | ≥10 µm: ≤6000 p/vial | Light obscuration particle count method.USP<788> | 3425 | 2810 | 1142 | 795 |
| | ≥25 µm: ≤600 p/vial | | 37 | 10 | 3 | 5 |
| Deliverable volumes | >100 ml | Volume measurement. USP<698> | NR. | N.R. | N.R. | 103 |
| Identification | | | | | | |
| Cysteine HCl*$H_2O$ | Same retention time | Liquid chromatography. | Complies | Complies | Complies | Complies |
| Ibuprofen | as standard | USP<621> | Complies | Complies | Complies | Complies |
| Acetaminophen | | | Complies | Complies | Complies | Complies |
| Acetaminophen content by HPLC | 95-105% | Eur.Ph 2.2.29; 0049 | 97 | 98 | 97 | 95 |
| Ibuprofen content by HPLC | 95-105% | Liquid chromatography. | 99 | 100 | 99 | 97.00 |
| Cysteine HCl*$H_2O$ by HPLC | Min 60% | USP<621> | 75% | 72% | 77% | 83% |
| Acetaminophen | | | | | | |
| Impurity K (4-aminophenol) | <0.05% | Eur.Ph 2.2.29; 0049 | 0.02 | 0.02 | 0.02 | 0.03 |
| Impurity F (4-nitrophenol) | <0.05% | | 0.00 | 0.00 | 0.00 | 0.00 |
| Any other impurity | <0.10% | | 0.01 | 0.01 | 0.01 | 0.01 |
| Total impurities | <0.2% | | 0.2 | 0.2 | 0.1 | 0.2 |
| Ibuprofen | | | | | | |
| Impurity A | <0.1% | Eur.Ph 2.2.29 | 0.0 | 0.0 | 0.0 | 0.0 |
| Impurity B | <0.2% | | 0.0 | 0.0 | 0.0 | 0.0 |
| Any other impurity | <0.10% | | 0.00 | 0.00 | 0.00 | 0.00 |
| Total impurities | <0.2% | | 0.0 | 0.0 | 0.0 | 0.0 |

TABLE 10 storage stability test - 3 mg/ml ibuprofen and 10 mg/ml paracetamol with cysteine (pH 6.6, 25 +/− 2° C., 40 +/− 5% relative humidity)

| Analysis | Specification | Method and Method No. | 1 month | 2 months | 3 months | 6 months |
|---|---|---|---|---|---|---|
| Appearance of solution | Clear liquid | Visual inspection. USP<641> | Complies | Complies | Complies | Complies |
| pH value | To be determined | Potentiometry. USP<791> | 6.96 | 6.95 | 7.02 | 7.00 |
| Coloration | ≤Y6 | Eur.Ph 2.2.2 | <Y6 | <Y6 | <Y6 | <Y6 |
| Sub visible particles | ≥10 μm: ≤6000 p/vial | Light obscuration particle | 3250 | 1690 | 2992 | 2407 |
|  | ≥25 μm: ≤600 p/vial | count method. USP<788> | 33 | 0 | 3 | 15 |
| Deliverable volumes | >100 ml | Volume measurement. USP<698> | N.R. | N.R. | N.R. | 102 |
| Identification |  |  |  |  |  |  |
| Cysteine HCl*H$_2$O | Same retention time | Liquid chromatography | Complies | Complies | Complies | Complies |
| Ibuprofen | as standard | USP<621> | Complies | Complies | Complies | Complies |
| Acetaminophen |  |  | Complies | Complies | Complies | Complies |
| Acetaminophen content by HPLC | 95-105% | Eur.Ph 2.2.29; 0049 | 103 | 103 | 103 | 100 |
| Ibuprofen content by HPLC | 95-105% | Liquid chromatography | 104 | 104 | 104 | 102 |
| Cysteine HCl*H$_2$O by HPLC | Min 60% | USP<621> | 90 | 85 | 90 | 91 |
| Acetaminophen |  |  |  |  |  |  |
| Impurity K (4-aminophenol) | <0.05% | Eur.Ph 2.2.29; 0049 | 0.02 | 0.02 | 0.02 | 0.02 |
| Impurity F (4-nitrophenol) | <0.05% |  | 0.00 | 0.00 | 0.00 | 0.00 |
| Any other impurity | <0.10% |  | 0.00 | 0.00 | 0.02 | 0.03 |
| Total impurities | <0.2% |  | 0.0 | 0.0 | 0.0 | 0.0 |
| Ibuprofen |  |  |  |  |  |  |
| Impurity A | <0.1% | Eur.Ph 2.2.29 | 0.0 | 0.0 | 0.0 | 0.0 |
| Impurity B | <0.2% |  | 0.0 | 0.0 | 0.0 | 0.0 |
| Any other impurity | <0.10% |  | 0.00 | 0.00 | 0.00 | 0.00 |
| Total impurities | <0.2% |  | 0.0 | 0.0 | 0.0 | 0.0 |

TABLE 11 storage stability test - 3 mg/ml ibuprofen and 10 mg/ml paracetamol with cysteine (pH 6.4, 25 +/− 2° C., 60 +/− 5% relative humidity)

| Analysis | Specification | Method and Method No. | Release | 1 month | 3 months | 6 months | 9 months | 12 months |
|---|---|---|---|---|---|---|---|---|
| Appearance of solution | Clear liquid | Visual inspection.USP<631>, Ph.Eur.2.2.1 | clear liquid | clear liquid | clear liquid | clear liquid | clear liquid | clear liquid |
| PH | 63-7,3 | Potentiometry.USP<791> Eur.Ph 2.2.3; Eur.Ph 2.9.17 | 6.4 | 6.6 | 6.8 | 6.9 | 6.9 | 6.9 |
| Coloration | ≤Y6 | Eur.Ph 2.2.2 | <Y6 | <Y5 | <Y5 | <Y5 | <Y5 | <Y5 |
| Particulate matter | ≥10 μm: ≤6000 p/vial | Light obscuration particle count | 2331 | 1083 | 229 | 148 | N.R. | 394 |
|  | ≥25 μm: ≤600 p/vial | USP<788>Ph.Eur.2.9.19 | 43 | 2 | 3 | 2 | N.R. | 2 |
| Identification |  |  |  |  |  |  |  |  |
| Ibuprofen | Same retention time as standard | USP<621>Ph.Eur.2.2.29 | Complies | Complies | Complies | Complies | Complies | Complies |
| Acetaminophen |  |  | Complies | Complies | Complies | Complies | Complies | Complies |
| Cysteine |  |  | Complies | Complies | Complies | Complies | Complies | Complies |
| Acetaminophen content (HPLC) | 95.0-105.0% | Eur.Ph 2.2.29; 0049 | 102.0% | 100.4% | 101.9% | 100.7% | 101.4% | 99.9% |
| Ibuprofen content (HPLC) | 95.0-105.0% | Liquid chromatography USP<621> In house-Ph.Eur.2.2.29 | 98.0% | 99.7% | 99.6% | 98.7% | 98.0% | 100.2% |
| Cysteine hydrochloride monohydrate (HPLC) | 80-105% at release Min 40% at s.h. | Liquid chromatography USP<621> In house-Ph.Eur.2.2.29 | 84% | 86% | 84% | 78.0% | 77.2% | 80.6% |

TABLE 11-continued storage stability test - 3 mg/ml ibuprofen and 10 mg/ml paracetamol with cysteine (pH 6.4,25 +/− 2° C., 60 +/− 5% relative humidity)

| Analysis | Specification | Method and Method No. | Release | 1 month | 3 months | 6 months | 9 months | 12 months |
|---|---|---|---|---|---|---|---|---|
| Impurities Acetaminophen | | | | | | | | |
| Impurity K (4-aminophenol) | ≤0.05% | Eur.Ph 2.2.29; 0049 | 0.020 | 0.021 | 0.020 | 0.025 | 0.028 | 0.030 |
| Impurity F (4-nitrophenol) | ≤0.05% | | 0.000 | 0.000 | 0.000 | 0.000 | 0.000 | 0.000 |
| Any other impurity | ≤0.10% | | 0.017 | 0.013 | 0.019 | 0.010 | 0.017 | 0.011 |
| Total impurities | ≤0.2% | | 0.037 | 0.035 | 0.039 | 0.035 | 0.045 | 0.041 |
| Impurities Ibuprofen | | | | | | | | |
| Impurity A | ≤0.1% | Eur.Ph 2.2.29 | 0.0 | 0.0 | 0.0 | 0.0 | 0.0 | 0.0 |
| Impurity B | ≤0.2% | | 0.0 | 0.0 | 0.0 | 0.0 | 0.0 | 0.0 |
| Any other impurity | ≤0.10% | | 0.00 | 0.00 | 0.00 | 0.00 | 0.00 | 0.00 |
| Total impurities | ≤0.2% | | 0.0 | 0.0 | 0.0 | 0.0 | 0.0 | 0.0 |

What is claimed is:

1. A method for treating pain comprising intravenously administering an aqueous analgesic composition comprising 2.8-3.2 mg/ml ibuprofen and 9.8-10.2 mg/ml paracetamol, wherein the aqueous analgesic composition has a pH at the time of preparation ($t_0$) that is between 6.3 and 6.8, inclusive and wherein the ibuprofen and the paracetamol remain in solution for at least 6 months at 25±2° C. and 40±5% relative humidity.

2. The method of claim 1, wherein the pH of the aqueous analgesic composition six months after the time of preparation is no higher than 7.3.

3. The method of claim 1, wherein the aqueous analgesic composition comprises an isotonic agent.

4. The method of claim 1, wherein the isotonic agent is mannitol.

5. The method of claim 1, wherein the aqueous analgesic composition comprises cysteine.

6. The method of claim 1, wherein the aqueous analgesic composition has dissolved oxygen content below 2 ppm.

7. The method of claim 1, wherein after one year of storage at 25±2° C. and 40±5% relative humidity, the aqueous analgesic composition comprises less than 0.05% wt/wt 4-aminophenol and less than 0.05% wt/wt 4-nitrophenol.

8. The method of claim 1, wherein the aqueous analgesic composition comprises 3 mg/ml ibuprofen and 10 mg/ml paracetamol.

* * * * *